United States Patent [19]

Chang et al.

[11] Patent Number: 4,684,646

[45] Date of Patent: Aug. 4, 1987

[54] 2-ACYLAMINOMETHYL-1,4-BENZODIAZEPINE DERIVATIVES AS CCK-ANTAGONISTS

[75] Inventors: Raymond S. L. Chang; Ben E. Evans, both of Lansdale, Pa.

[73] Assignee: Merck & Co., Inc., Rahway, N.J.

[21] Appl. No.: 799,050

[22] Filed: Nov. 18, 1985

Related U.S. Application Data

[63] Continuation of Ser. No. 624,841, Jun. 26, 1984, abandoned.

[51] Int. Cl.$^4$ ............................................. A61K 31/55
[52] U.S. Cl. ..................................................... 514/221
[58] Field of Search ......................................... 514/221

[56] References Cited

U.S. PATENT DOCUMENTS

| | | | |
|---|---|---|---|
| 3,738,999 | 6/1973 | Krapcho et al. | 260/347.3 |
| 3,947,475 | 3/1976 | DeBaun et al. | 260/347.3 |
| 3,998,809 | 12/1976 | Milkowski et al. | 260/239 BD |
| 4,096,141 | 6/1978 | Milkowski et al. | 260/239 BD |
| 4,325,957 | 4/1982 | Zeugner et al. | 514/213 |
| 4,474,777 | 10/1984 | Cassal et al. | 424/244 |
| 4,482,548 | 11/1984 | Roemer et al. | 424/244 |
| 4,487,771 | 12/1984 | Buglioni | 424/244 |
| 4,533,662 | 8/1985 | Zeugner et al. | 514/221 |

FOREIGN PATENT DOCUMENTS

| | | | |
|---|---|---|---|
| 0054839 | 6/1982 | European Pat. Off. | 514/221 |
| 2952279 | 6/1981 | Fed. Rep. of Germany | 514/221 |
| 1438204 | 6/1976 | United Kingdom | 514/221 |

OTHER PUBLICATIONS

Chem. Abst. 95:169234(b) (1981)–Zeugner et al.
Chem. Abst. 97:216246(k) (1982)–Zeugner et al.
Chem. Abst. 100:564(v) (1984)–Morley et al.
Chem. Abst. 100:18425k (1984)–Morley et al.

*Primary Examiner*—Douglas W. Robinson
*Attorney, Agent, or Firm*—Samuel B. Abrams; Hesna J. Pfeiffer

[57] ABSTRACT

A method of antagonizing the function of cholecystokinins in a disease state in mammals, especially in humans, which comprises administering a pharmaceutically-effective amount of certain 2-acylaminomethyl-1,4-benzodiazepine derivatives or their salts, alone or with a pharmaceutical carrier, with or without an adjuvant.

2 Claims, No Drawings

2-ACYLAMINOMETHYL-1,4-BENZODIAZEPINE DERIVATIVES AS CCK-ANTAGONISTS

This is a continuation of U.S. patent application, Ser. No. 624,841, filed June 26, 1984, now abandoned.

The present invention is directed to a method of antagonizing the function, particularly the excessive function, of cholecystokinins (CCK) in a disease state in mammals, especially in humans, which comprises administering a pharmaceutically-effective amount of certain 2-acylaminomethyl-1,4-benzodiazepine derivatives of their salts, alone or with a pharmaceutical carrier, with or without an adjuvant.

BACKGROUND OF THE INVENTION

Cholecystokinins (CCK) are neuropeptides (see, Mutt and Jorpes, *Biochem. J.*, 125, 678 (1971)) which exist in both gastrointestinal tissue and the central nervous system (V. Mutt, *Gastrointestinal Hormones*, G. B. J. Glass, ed., Raven Press, N.Y., 1980, p. 169), and include, e.g., CCK-33, a neuropeptide of thirty-three aminoacids, and CCK-8, a carboxyl-terminal octapeptide. These molecules are believed to be physiological satiety hormones and, therefore, may play an important role in appetite regulation (G. P. Smith, *Eating and Its Disorders*, A. J. Stunkard and E. Stellar, Eds., Raven Press, New York, 1984, p. 67).

In addition, CCK's stimulate colonic motility, gall bladder contraction, and pancreatic enzyme secretion, and inhibit gastric emptying. CCK's reportedly also co-exist with dopamine in certain mid-brain neurons, and thus may additionally play a role in the functioning of dopaminergic systems in the brain, as well as serve as neurotransmitters in their own right. See: A. J. Prange et al., "Peptides in the Central Nervous System", *Ann. Repts. Med. Chem.*, 17, 31, 33 (1982), and references cited therein; J. A. Williams, *Biomed. Res.*, 3, 107 (1982); and J. E. Morley, *Life Sci.*, 30, 479 (1982).

Antagonists of CCK have been useful for preventing or treating CCK-related disorders of the gastrointestinal, central nervous and appetite regulatory systems of animals, especially of humans. Three distinct chemical classes of CCK-receptor antagonists have been reported. The first class comprises derivatives of cyclic nucleotides, of which dibutyryl cyclic GMP has been known to be the most potent by detailed structure-function studies (see, N. Barlos et al., *Am. J. Physiol.*, 242, G161 (1982) and P. Robberecht et al., *Mol. Pharmacol.*, 17, 268 (1980)). The second class comprises peptide antagonists which are C-terminal fragments and analogs of CCK, of which both shorter (Boc-Met-Asp-Phe-NH$_2$, Met-Asp-Phe-NH$_2$) and longer (Cbz, Tyr(SO$_3$H)-Met-Gly-Trp-Met-Asp-NH$_2$) C-terminal fragments of CCK can function as CCK antagonists, according to recent structure-function studies, (see, R. T. Jensen et al., *Biochim. Biophys. Acta.*, 757, 250 (1983), and M. Spanarkel et al., *J. Biol. Chem.*, 258, 6746 (1983)). Then, the third class of CCK receptor antagonists comprises the amino acid derivatives: proglumide, a derivative of glutaramic acid, and the N-acyl tryptophans, including para-chlorobenzoyl-L-tryptophan (benzotript), (see, W. F. Hahne et al., *Proc. Natl. Acad. Sci. U.S.A.*, 78, 6304 (1981) and R. T. Jensen et al., *Biochim. Biophys. Acta.*, 761, 269 (1983)). All of these compounds, however, are relatively weak antagonists of CCK (IC$_{50}$: generally $10^{-4}$M, but down to $10^{-6}$M in the case of the peptides) and the peptide CCK-antagonists have substantial stability and absorption problems.

It was, therefore, an object of this invention to identify substances which more effectively antagonize the function, especially the excessive function, of cholecystokinins in disease states in mammals, especially in humans. It was also an object of this invention to develop a method of preventing or treating CCK-related disorders of the gastrointestinal, central nervous and appetite regulatory systems of mammals, especially humans.

SUMMARY OF THE INVENTION

The instant invention is directed to the use of certain 2-acylaminomethyl-1,4-benzodiazepine derivatives or salts of these derivatives for antagonizing the function of cholecystokinins in disease states in mammals, especially in humans.

DETAILED DESCRIPTION OF THE INVENTION

Applicants have surprisingly discovered that certain 2-acylaminomethyl-1,4-benzodiazepine derivatives of formula I, disclosed in U.S. Pat. No. 4,325,957, to Zeugner et al. (the contents of which are included by reference):

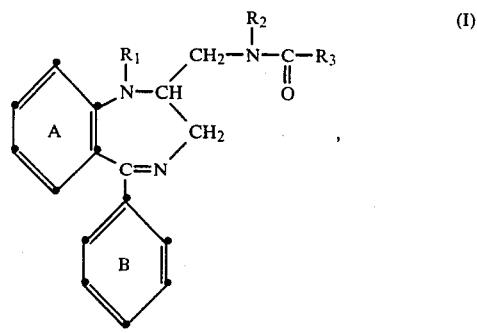

wherein:
R$_1$ represents hydrogen, straight or branched chain C$_{1-4}$-alkyl or C$_{1-4}$-alkenyl, or cyclopropylmethyl;
R$_2$ represents hydrogen, or straight or branched chain C$_{1-4}$-alkyl or C$_{1-4}$-alkenyl;
R$_3$ represents a group of the formula a, b, c, d or additionally, e:

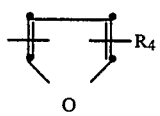

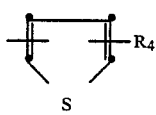

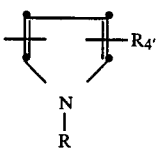

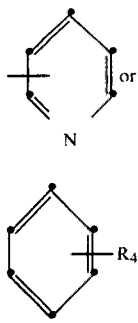

wherein
R is hydrogen or $C_{1-3}$-alkyl;
$R_4$ is hydrogen, straight or branched chain $C_{1-4}$-alkyl, or $C_{1-4}$-alkoxy, nitro or chlorine, fluorine, or bromine;
$R_{4'}$ is hydrogen or $C_{1-4}$-alkyl;
and the aromatic groups, A and B, independently, may be unsubstituted or substituted by 1 to 3 substituents selected from the group consisting of Cl, Br or F, $C_{1-4}$-alkylthio, $C_{1-4}$-alkoxy, $C_{1-4}$-alkyl, hydroxy, nitro and trifluoromethyl, or may be substituted at two adjacent carbon atoms by methylenedioxy or ethylenedioxy,
or optical isomers or pharmaceutically-acceptable salts thereof, antagonize the function, particularly the excessive function of cholecystokinins in disease states in mammals, especially in humans.

Preferred compounds for antagonizing the function of CCK according to the instant invention include, e.g., those wherein the $C_{1-4}$-alkyl or -alkenyl groups of $R_1$, $R_2$, $R_4$ or the substituents of aromatic groups A and/or B, represent methyl, ethyl, propyl, isopropyl, n-butyl, 1-methylpropyl, 2-methylpropyl, tert.-butyl, allyl, 2-butenyl or 3-butenyl; or, if the aromatic rings A and/or B are di- or tri-substituted, then the substituents are methyl or ethyl groups; or, if alkylthio, nitro or trifluoromethyl groups are substituted on either or both rings, monosubstitution is preferred; or, if Cl, F or Br and/or alkyl, and/or hydroxy groups are substituted on either or both rings, mono- or di-substitution is preferred; or, if alkoxy groups, particularly methoxy groups are substituted, then tri-substitution is preferred.

Particularly preferred compounds according to the instant invention include compounds taken from the group consisting of (−)-1-methyl-2-(thiophene-3-carbonyl)aminomethyl-5-(2'-fluorophenyl)-1H-2,3-dihydro-1,4-benzodiazepine; 1-methyl-2-(4'-chlorophenylcarbonyl)aminoethyl-5-(2'-fluorophenyl)-1H-2,3-dihydro-1,4-benzodiazepine; (±)-1-methyl-2-(thiophene-3-carbonyl)aminomethyl-5-(2'-fluorophenyl)-1H-2,3-dihydro-1,4-benzodiazepine; 1-methyl-2-(4'-chlorophenylcarbonyl)aminomethyl-5-(2'-fluorophenyl)-1H-2,3-dihydro-1,4-benzodiazepine; 1-methyl-2-(2'-fluorophenylcarbonyl)aminomethyl-5-(2'-fluorophenyl)-1H-2,3-dihydro-1,4-benzodiazepine; [(1-methyl-5-(2'-fluorophenyl)-1H-1,4-benzopin-2-yl)methyl]-1H-isoindole-1,3-(2H)-dione; (+)-1-methyl-2-(thiophene-3-carbonyl)aminomethyl-5-(2'-fluorophenyl)-1H-2,3-dihydro-1,4-benzodiazepine; and 1-methyl-2-(pyridine-3-carbonyl)aminomethyl-5-(2'-fluorophenyl)-1H-2,3-dihydro-1,4-benzodiazepine, which have the formula:

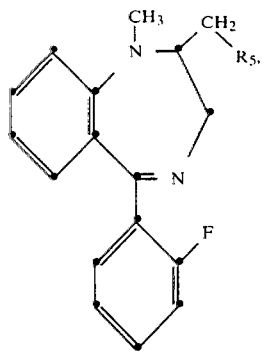

wherein $R_5=$

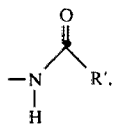

where $R'=$

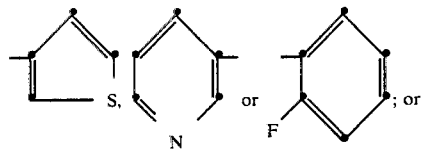

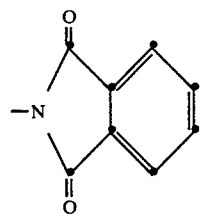

or pharmaceutically-acceptable salts thereof.

The pharmaceutically-acceptable salts of the compounds of the instant invention include the conventional non-toxic salts or the quarternary ammonium salts of the compounds of this invention, which are formed, for example, from non-toxic inorganic or organic acids. For example, such conventional non-toxic salts include those derived from inorganic acids, such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, theophylline, 8-chlorotheophylline, p-aminobenzoic, p-acetamidobenzoic, methanesulfonic, ethane disulfonic, oxalic, isethionic, and the like.

Certain 2-acylaminomethyl-1H-2,3-dihydro-1,4-benzodiazepine derivatives were disclosed in U.S. Pat. No. 4,325,957. However, those derivatives were suggested as possessing strong analgesic activities, in addition to psychopharmacological, diuretic and antiarrythmic properties. Additionally, the compound, where

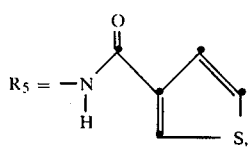

has been reported to be an opiate-agonist with selectivity for the kappa receptor (see, D. Roemer et al., *Nature*, 298, 759 (1982)) and its (−)-enantiomer is preferred for high analgesic activity (see, H. Kley et al., *Eur. J. Pharmacol.*, 87, 503 (1983)). This compound has also been shown to increase food intake in rats (see, J. E. Morley et al., *Eur. J. Pharmacol.*, 93, 265 (1983)). However, it has not previously been known that any of the compounds according to the formula of the instant invention would antagonize the function, particularly the excessive function, of cholecystokinin in a disease state in mammals.

Screening of these known compounds to determine biological activity and obtain an $IC_{50}$ value for them to identify significant CCK-antagonism may be accomplished using an $^{125}I$-CCK receptor binding assay and in vitro isolated tissue preparations. These tests involve the following:

CCK RECEPTOR BINDING (PANCREAS) METHOD

CCK-33 was radiolabeled with $^{125}I$-Bolton Hunter reagent (2000 Ci/mmole), as described by Sankara et al. (*J. Biol. Chem.*, 254, 9349–9351, 1979). Receptor-binding was performed according to Innis and Snyder (*Proc. Natl. Acad. Sci.*, 77, 6917–6921, 1980), with the minor modification of adding the additional protease inhibitors, phenyl-methane sulfonyl fluoride and o-phenanthroline, which have no effect on the $^{125}I$-CCK receptor binding assay.

The whole pancreas of a male Sprague-Dawley rat (200–350 g), which had been sacrificed by decapitation, was dissected free of fat tissue and homogenized in 20 volumes of ice-cold 50 mM Tris HCl (pH 7.7 at 25° C.) with a Brinkmann Polytron PT-10. The homogenates were centrifuged at 48,000 g for 10 minutes, then the resulting pellets were resuspended in Tris Buffer, centrifuged as above, and resuspended in 200 volumes of binding assay buffer (50 mM Tris HCl, pH 7.7 at 25° C., 5 mM dithiothreitol, 0.1 mM bacitracin, 1.2 mM phenylmethane sulfonyl fluoride and 0.5 mM o-phenanthroline).

For the binding assay, 25 μl of buffer (for total binding), or unlabeled CCK-8 sulfate sufficient to give a final concentration of 1 μM of CCK-8 (for nonspecific binding), or the compounds of the formula of the compounds according to the instant invention (for determination of antagonism to $^{125}I$-CCK binding) and 25 μl of $^{125}I$-CCK-33 (30,000–40,000 cpm), were added to 450 μl of the membrane suspensions in microfuge tubes. All assays were run in duplicate of triplicate, and the reaction mixtures were incubated at 37° C. for 30 minutes and centrifuged in a Beckman Microfuge (4 minutes) immediately after adding 1 ml of ice-cold incubation buffer. The supernatant was aspirated and discarded, and the pellets were counted with a Beckman gamma 5000. For Scatchard analysis to determine the mechanism of inhibition of $^{125}I$-CCK binding by the most potent compounds (*Ann. N.Y. Acad. Sci.*, 51: 660, 1949), $^{125}I$-CCK-33 was progressively diluted with increasing concentrations of CCK-33.

ISOLATED GUINEA PIG GALL BLADDER METHOD

The two halves of the gall bladders, free of adjacent tissue, of male Hartley guinea pigs (400–600 g), which had been sacrificed by decapitation, were suspended under 1 g tension along the axis of the bile duct in 5 ml organ bath, containing a Kreb's bicarbonate solution of 118 mM NaCl, 4.75 mM KCl, 2.54 $CaCl_2$, 1.19 mM $KH_2PO_4$, 1.2 mM $MgSO_4$, 25 mM $NaHCO_3$ and 11 mM dextrose, which is maintained at 32° C. and bubbled with a mixture of 95% $O_2$ and 5% $CO_2$. The tissues were washed every 10 minutes for 1 hour to obtain equilibrium prior to the beginning of the study and the isometric contractions of the strips were recorded using Statham (60 g:0.12 mm) strain gauges and a Hewlett-Packard 77588 recorder.

CCK-8 was added cumulatively to the baths and the $EC_{50}$'s were determined using regression analysis. After washout (every 10 minutes for 1 hour), the compound to be tested was added at least 5 minutes before the addition of CCK-8 and the $EC_{50}$ of CCK-8 in the presence of the compound to be tested was also similarly determined.

IN VITRO EFFECT OF THE COMPOUNDS ACCORDING TO THIS INVENTION ON $^{125}I$-CCK-33 RECEPTOR BINDING AND ON CCK-8 RESPONSE IN GUINEA PIG GALL BLADDER

The compounds of the instant invention inhibited specific $^{125}I$-CCK-33 binding in a concentration-dependent manner, generally with an $IC_{50}$ less than or equal to 100 μM. Scatchard analysis of specific $^{125}I$-CCK-33 receptor binding in the absence and presence of 0.2 μM of (±)-1-methyl-2-[thiophene-3-carbonylaminomethyl]-5-(2-fluorophenyl)-1H-2,3-dihydro-1,4-benzodiazepine indicated this compound competitively inhibited specific $^{125}I$-CCK-33 receptor binding since it increased the $K_D$ (dissociation constant) without affecting the $B_{max}$ (maximum receptor number). The $K_i$ value (dissociation constant of inhibitor) of the compounds of this invention was estimated to be 0.25 μM.

In the guinea pig gall bladder test, (±)-1-methyl-2-(thiophene-3-carbonyl)aminomethyl-5-(2'-fluorophenyl)-1H-2,3-dihydro-1,4-benzodiazepine (2 μM) caused a parallel shift to the right of the CCK dose response curve without reduction of the maximal contractile response, indicating competitive antagonism of CCK.

The ability of the compounds of the instant invention to antagonize CCK makes these compounds useful as pharmaceutical agents for mammals, especially for humans, for the treatment and prevention of disorders wherein CCK may be involved. Examples of such disease states include gastrointestinal disorders, especially such as irritable bowel syndrome or ulcers, excess pancreatic or gastric secretion, acute pancreatis, or motility disorders; central nervous system disorders, caused by CCK interaction with dopamine, such as neuroleptic disorders, tardive dyskinesia, Parkinson's disease, psychosis or Gilles de la Tourette Syndrome; and disorders of appetite regulatory systems.

The compounds of the instant invention or pharmaceutically-acceptable salts thereof, may be administered to a human subject either alone or, preferably, in combination with pharmaceutical composition, according to standard pharmacetical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramusclar, intraperitoneal, subcutaneous and intravenous use, sterile solution of the active ingredient are usually prepared, and the pH of the solutions should be suitable adjusted and buffered. For intravenous use, the total concentration of solutes should be controlled to render the preparation isotonic.

When a compound according to the instant invention or a salt thereof, is used as an antagonist of CCK in a human subject, the daily dosage will normally be determined by the prescribing physician. Moreover, the dosage will vary according to the age, weight, and response of the individual patient, as well as the severity of the patient's symptoms. However, in most instances, an effective daily dosage will be in the range of from about 0.05 mg/kg to about 100 mg/kg, and preferably, of from 0.5 mg/kg to about 20 mg/kg administered in single or divided doses. In some cases, however, it may be necessary to use dosages outside these limits.

Synthesis of the compounds according to the instant invention may be according to the procedures described in U.S. Pat. No. 4,325,957, W. Milkowski et al, Eur. J. Med. Chem., 11, (6) 501, 1976, and D. Roemer et al., Nature, 298, 759, 1982, or other acceptable procedure.

The pharmaceutically-acceptable salts of the present invention may be synthesized from the compounds according to the instant invention, which contain a basic or acidic moiety, by conventional chemical methods. Generally, the salts are prepared by reacting the free base or free acid with stoichiometric amounts of or with an excess of the desired salt-forming inorganic or organic acid or base in a suitable solvent or in various combinations of solvents. The pharmaceutically-acceptable salts of the acids according to this invention are also readily prepared by conventional procedures such as treating an acid of this invention with an appropriate amount of a base, such as an alkali or alkaline earth metal hydroxide, e.g., sodium, potassium, lithium, calcium, or magnesium, or an organic base such as an amine, e.g., dibenzylethylenediamine, trimethylamine, piperidine, pyrrolidine, benzylamine, and the like.

This invention is further defined by reference to the following example which is intended to be illustrative and not limiting.

EXAMPLE 1

CCK Activity Assessment (−)-1-methyl-2-(thiophene-3-carbonyl)aminomethyl-5-(2′-fluorophenyl)-1H-2,3-dihydro-1,4-benzodiazepine, [1]; (±)-1-methyl-2-(thiophene-3-carbonyl)aminomethyl-5-(2′-fluorophenyl)-2,3-dihydro-1,4-benzodiazepine, [2]; 1-methyl-2-(4′-chlorophenylcarbonyl)aminomethyl-5-(2′-fluorophenyl)-1H-2,3-dihydro-1,4-benzodiazepine, [3]; 1-methyl-2-(2-fluorophenylcarbonyl)aminomethyl-5-(2′-fluorophenyl)-1H-2,3-dihydro-1,4-benzodiazepine, [4]; [(1-methyl-5-(2′-fluorophenyl)-1H-1,4-benzopin-2-yl)methyl]-1H-isoindole-1,3-(2H)-dione, [5]; (+)-1-methyl-2-(thiophene-3-carbonyl)aminomethyl-5-(2-fluorophenyl)-1H-2,3-dihydro-1,4-benzodiazepine, [6]; and 1-methyl-2-(pyridine-3-carbonyl)aminomethyl-5-(2′-fluorophenyl)-1H-2,3-dihydro-1,4-benzodiazepine, [7], prepared according to the procedure described in W. Milkowski et al., Eur. J. Med. Chem.—Chimica Therapeutica, 11, v. 6, 501, 1976, were tested for antagonism to CCK receptor binding in the pancreas using the method described above, with the following results:

| Compound | IC$_{50}$ ($\mu$M) CCK Pancreas |
|---|---|
| 1 | 0.1 |
| 2 | 0.2 |
| 3 | 0.8 |
| 4 | 2.9 |
| 5 | 4.3 |
| 6 | 13.9 |
| 7 | 10.0 |

The IC$_{50}$ values (the concentrations required to cause inhibition of 50% of the $^{125}$I-CCK binding) in the pancreas demonstrate the compounds of the present invention are from about 10 times to about 1000 times more potent than previously known compounds, and thus demonstrate significantly improved antagonism to the function of CCK.

What is claimed is:

1. A method of antagonizing the binding of cholecystokinins to cholecystokinin receptors in a mammal which comprises contacting said cholecystokinin receptors with a compound represented by the formula:

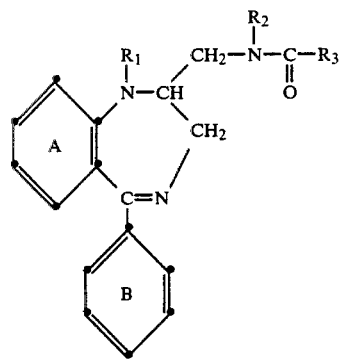

wherein:

R$_1$ represents hydrogen, straight or branched chain C$_{1-4}$-alkyl or C$_{1-4}$-alkenyl, or cyclopropylmethyl;

R$_2$ represents hydrogen, or straight or branched chain C$_{1-4}$-alkyl or C$_{1-4}$-alkenyl;

R$_3$ represents a group of the formula a, b, c, d or e:

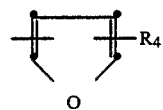

-continued

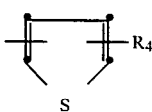

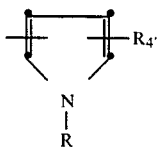

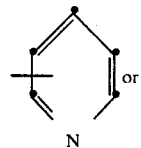

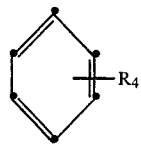

wherein:

R is hydrogen or $C_{1-3}$-alkyl;

$R_4$ is hydrogen, straight or branched chain $C_{1-4}$-alkyl, or $C_{1-4}$-alkoxy, nitro or chlorine, fluorine, or bromine;

$R_4'$ is hydrogen or $C_{1-4}$-alkyl;

and the aromatic groups, A and B, independently, may be unsubstituted or mono-, di- or tri-substituted where the substituents are selected from the group consisting of Cl, Br, F, $C_{1-4}$-alkylthio, $C_{1-4}$-alkoxy, $C_{1-4}$-alkyl, hydroxy, nitro, and trifluoromethyl, and pharmaceutically-acceptable salts thereof.

2. The method in accordance with claim 1 wherein said compound is selected from the group consisting of:

(−)-1-methyl-2-(thiophene-3-carbonyl)aminomethyl-5-(2'-fluorophenyl)-1H-2,3-dihydro-1,4-benzodiazepine;

(±)-1-methyl-2-(thiophene-3-carbonyl)aminomethyl-5-(2'-fluorophenyl)-1H-2,3-dihydro-1,4-benzodiazepine;

1-methyl-2-(4'-chlorophenylcarbonyl)-aminomethyl-5-(2'-fluorophenyl)-1H-2,3-dihydro-1,4-benzodiazepine;

1-methyl-2-('2-fluorophenylcarbonyl)aminomethyl-5-(2'-fluorophenyl)-1H-2,3-dihydro-1,4-benzodiazepine;

2-[(2,3-dihydro-1-methyl-5-(2'-fluorophenyl)-1H-1,4-benzopin-2-yl)-methyl]-1H-isoindole-1,3-(2H)-dione;

(+)-1-methyl-2-(thiophene-3-carbonyl)aminomethyl-5-(2'-fluorophenyl)-1H-2,3-dihydro-1,4-benzodiazepine;

1-methyl-2-(pyridine-3-carbonyl)aminomethyl-5-(2'-fluorophenyl)-1H-2,3-dihydro-1,4-benzodiazepine, and pharmaceutically acceptable salts thereof.

* * * * *